(12) United States Patent
Hale

(10) Patent No.: US 11,413,111 B2
(45) Date of Patent: Aug. 16, 2022

(54) AUGMENTED REALITY SYSTEM FOR MEDICAL PROCEDURES

(71) Applicant: Karl Storz Imaging, Inc., Goleta, CA (US)

(72) Inventor: Eric L. Hale, Goleta, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 227 days.

(21) Appl. No.: 16/422,471

(22) Filed: May 24, 2019

(65) Prior Publication Data

US 2020/0367990 A1   Nov. 26, 2020

(51) Int. Cl.
| | |
|---|---|
| *G02B 27/01* | (2006.01) |
| *A61B 90/00* | (2016.01) |
| *A61B 90/50* | (2016.01) |
| *A61B 5/00* | (2006.01) |
| *G06T 19/00* | (2011.01) |

(52) U.S. Cl.
CPC ............ *A61B 90/361* (2016.02); *A61B 90/37* (2016.02); *A61B 90/50* (2016.02); *G02B 27/017* (2013.01); *A61B 5/7445* (2013.01); *A61B 2090/365* (2016.02); *A61B 2090/502* (2016.02); *G02B 2027/0112* (2013.01); *G02B 2027/0141* (2013.01); *G02B 2027/0178* (2013.01); *G06T 19/006* (2013.01)

(58) Field of Classification Search
CPC ..... G02B 27/017; A61B 90/361; A61B 90/37; G06T 18/006
See application file for complete search history.

(56) References Cited

U.S. PATENT DOCUMENTS

| | | | |
|---|---|---|---|
| 6,847,336 B1* | 1/2005 | Lemelson | G16H 20/40 345/8 |
| 10,646,283 B2* | 5/2020 | Johnson | G06F 3/011 |
| 2014/0081659 A1* | 3/2014 | Nawana | A61B 5/1118 705/3 |
| 2014/0139405 A1* | 5/2014 | Ribble | A61G 7/002 345/8 |
| 2016/0225192 A1* | 8/2016 | Jones | G06F 3/012 |
| 2019/0075230 A1* | 3/2019 | Takeda | H04N 5/232933 |
| 2019/0133689 A1* | 5/2019 | Johnson | G06F 3/0346 |

* cited by examiner

*Primary Examiner* — Kevin M Nguyen
(74) *Attorney, Agent, or Firm* — Whitmyer IP Group LLC

(57) ABSTRACT

A system for displaying medical data is provided having a source providing image data, a monitor presenting the image data, a plurality of medical devices generating signals each indicative of a medical parameter, and a display for presenting at least one signal correlated with a view vector of the display.

22 Claims, 2 Drawing Sheets

AUGMENTED REALITY SYSTEM FOR MEDICAL PROCEDURES

TECHNICAL FIELD

The present teachings relate generally to an augmented reality system for medical procedures, and more specifically to displaying medical parameters in endoscopic camera systems using augmented reality.

BACKGROUND

Modern medical systems rely on ever-growing amounts of information. Measurements, readings, images, notes, and other information is constantly generated and recorded while giving care to a patient. Real-time display of and action based on this information can be critical to providing safe and effective care.

For example, a surgeon performing a minimally invasive surgery must keep track of not only the video from an endoscopic camera, but also be aware of and control current medical parameters. Patient status information such as biographical information, heart rate, blood pressure, and oxygen levels may be essential for a surgeon to quickly and easily monitor or know. A surgeon may also want to know the real-time status of devices such as endoscopic cameras, pumps, insufflators, and other surgical devices. A medical professional reviewing a patient file or remotely consulting on a surgery may also want to view medical parameters while viewing medical images from a prior or occurring procedure. Surgeons and medical professionals may also want to act on information by controlling or adjusting settings or parameters of devices.

However, presenting medical parameters on the monitor at the same time as the endoscopic video reduces the display area available for the high-resolution endoscopic video. While a second or larger monitor could be used to display medical parameters, this would require that a medical processional make gross movements and look away from the endoscopic video, and would further crowd the operating room. Further, current systems do not provide an adequate solution for multiple medical professionals that would like to view the same or different medical parameters simultaneously. Finally, while visual or audio alerts can be used to tell a medical professional that a medical parameter is outside of a normal range, they will still need to look at a screen to see the actual measured value.

In addition, controlling medical devices currently requires either physically touching the device or a touchscreen. While voice commands can be used to control medical devices, a medical professional must first make a gross movement to view a screen to view current parameters to know whether to issue a voice command. Otherwise, the medical professional must wait for a response to a voice query to know the current medical parameters before making an adjustment.

Therefore, among other objectives, it would be beneficial to have an alternative system and method for displaying medical parameters in endoscopic camera systems.

It would also be beneficial to have a system that does not require a gross movement to view medical parameters.

It would also be beneficial to have a system that shows medical parameters to a user, even when the user is moving.

In addition, it would be beneficial to have a system that dynamically changes the medical parameters displayed based on what the user is viewing at a given time.

Further, it would be beneficial to have a system that dynamically determines the best location to medical parameters.

It would also be beneficial for a system that allows adjustment of medical parameters through device control.

These and other objectives would be known and understood by a person having ordinary skill in the art.

SUMMARY

The needs set forth herein as well as further and other needs and advantages are addressed by the present embodiments, which illustrate solutions and advantages described below.

The disclosed system includes, but is not limited to, a source providing image data, a monitor presenting the image data, a plurality of medical devices generating signals each indicative of a medical parameter, and a display for presenting at least one signal correlated with a view vector of the display.

In an embodiment of the disclosed system, an endoscopic camera provides a real-time video to a monitor. Heart rate monitors, oxygen sensors, pumps, insufflators, and/or other devices provide medical parameters to be displayed using augmented reality glasses.

A view vector of a user of the system is determined in order to select and display medical parameters. The view vector can be determined and/or refined in multiple ways. For example, the view vector can extend from a pair of augmented reality glasses. The view vector can also be based on the eye movements of the user. In addition, positional sensors such as accelerometers or gyroscopes can be used to determine the view vector.

A controller analyzes images from a camera to determine whether icons, marks, objects, symbols, or other identifiers (hereinafter collectively, "identifiers") appear in the view vector. Different identifiers in the view vector cause different information to be displayed. For example, a view vector correlated with a top-left corner of a monitor may cause device status information to appear along with a menu for controlling the devices. Alternatively, a view vector correlated with a medical device such as a pump causes pump-related information and controls may be displayed. Further, various anatomy may cause information regarding that anatomy to be displayed. For instance, if looking at a heart, general medical information regarding a heart, or information regarding the particular patient, including current heart status information such as heart rate, may be displayed. Identifiers may be physical (including a person or a medical device) or displayed be on the monitor. In addition, a view vector may cause an ideal or reference image to be displayed. The ideal or reference image may show what a body part should look like or how a body part should be aligned during surgery. Ideal or reference images may be from stock photographs or may be personalized to the patient (i.e., from previous imaging or surgeries.) In one embodiment, a surgeon may be able to follow along with ideal or reference images, which may include instructions or steps for the surgery. Furthermore, a view vector may cause a gauge to be displayed for showing information. In one example, the gauge can show a rotation of the endoscopic camera relative to the body.

Based on the view vector, the controller determines a region in the augmented reality glasses to display medical parameters. As the user moves or rotates, so will the region such that it remains "snapped" in place. Alliteratively, medical parameters may be displayed in a periphery of the augmented reality glasses. For example, the wearer may simply look down to view medical parameters.

If the region used for display would overlap objects, such as the monitor, the controller may resize or reposition the region used for display so that it does not overlap. Alternatively, the controller may select a different region to use for display. Repositioning and resizing can also prevent the augmented reality display from blocking safety-critical objects and information.

Based on the view vector, control of medical devices can be effectuated. For example, the view vector can be used as a mouse to select menu options displayed on the monitor or can be used to start voice control. In addition, menus can be displayed and selectable on the alternative reality glasses. Any medical device or other device can be controlled, including pumps, insufflators, endoscopic cameras, shavers, AN routers, room cameras, room lights, blinds, shades, speakers, monitors, any central operating room controllers, etc.

Other embodiments of the system are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION

The present teachings are described more fully hereinafter with reference to the accompanying drawings, in which the present embodiments are shown. The following description is presented for illustrative purposes only and the present teachings should not be limited to these embodiments. Any computer configuration and architecture satisfying the speed and interface requirements herein described may be suitable for implementing the system of the present embodiments.

Figure 1:
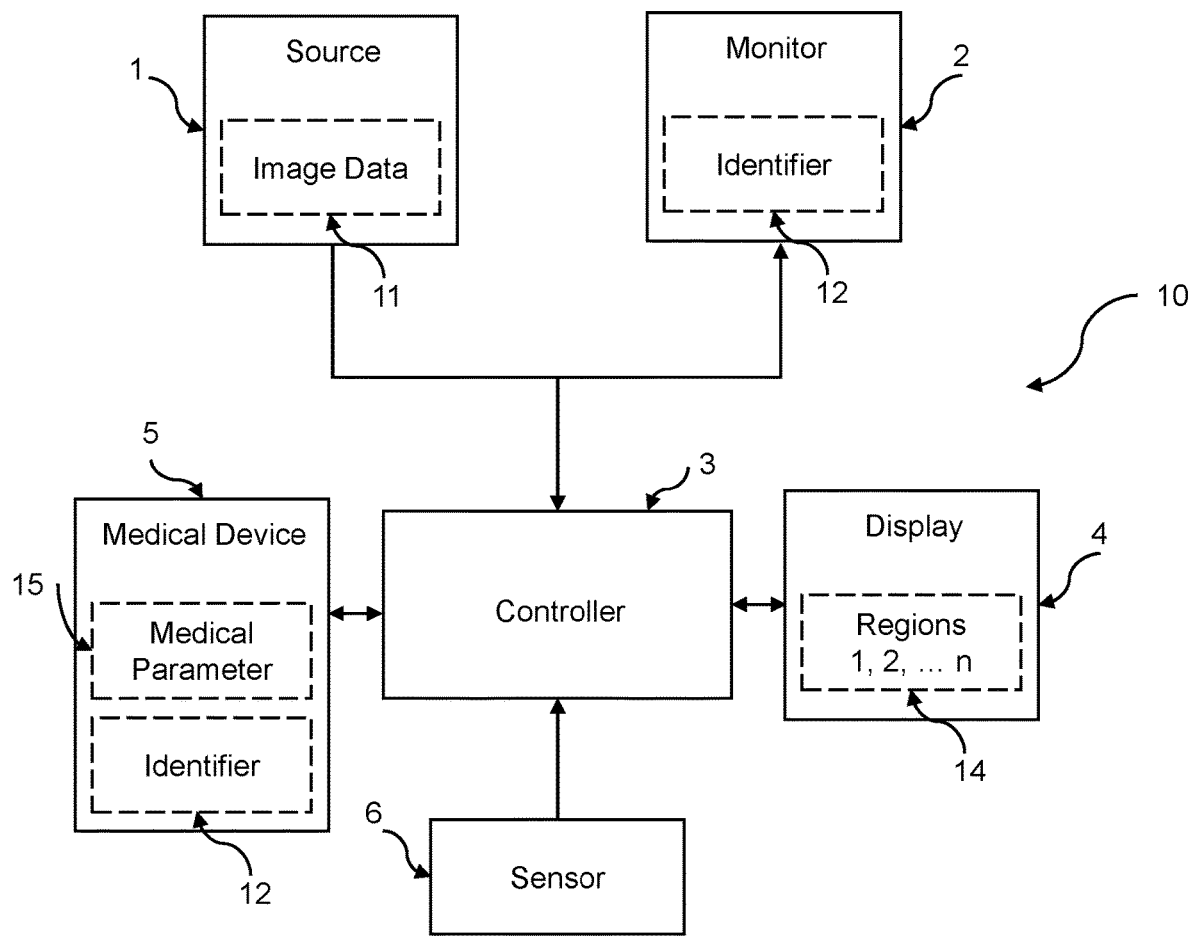
FIG. 1 is a schematic drawing of the inventive system.

Referring to FIG. 1, an augmented reality system 10 for medical procedures is shown. The system 10 has an image source 1, which provides image data 11 to a monitor 2. The system 10 has a controller 3, which receives medical parameters 15 from at least one medical device 5. Connections between devices in system 10 can be wired, wireless, or a combination of both.

The medical parameters 15 are displayed in at least one region 14 of display 4. The medical parameters 15 may be selectively displayed based on a view vector of display 4 or a user of the system. Regions 14 may be selectively used to display medical parameters 15 based on the view vector of the display 4. A sensor 6 may be used determine the view vector of display 4 or a user of the system.

A source 1 may include any devices, systems, or networks that generate, acquire, store, monitor, or control image data, such as still images or video. Sources 1 may include common types of operating room cameras, including endoscopic cameras, video endoscopes, room cameras, light cameras, and boom cameras. In addition, sources may include any recording, storage, and/or archival devices or systems, such as screen splitters, quad image controllers, recording devices, image capture devices, PACS (Picture Archiving and Communication System) computers, a DICOM system, or a hospital information system. Sources 1 may also include other devices from which image data may be received, such as a central computer for controlling various devices, or auxiliary inputs for connecting external devices. Sources 1 may also receive image data from other sources. For example, a source may provide video to a recording device, which in turn becomes a source to the system.

A monitor 2 may include any devices, systems or networks that present image data, or otherwise communicate image data to viewers. A monitor 2 may include any of various presentation devices, such as a flat panel, an LED TV, an OLED TV, a plasma screen, a projector, or a computer monitor. A monitor 2 may also include presentation devices that have unconventional formats, such as full wall projectors.

The source 1 may provide image data to the monitor 2 through a wired or wireless connection. For example, an integrated operating room may feature a direct connection between an endoscopic camera and a flat panel. Alternatively, a source 1 may provide image data to a monitor 2 through an intermediate controller, computer, or network. For example, an endoscopic camera may provide video to an audio-visual router, which in turn provides that video to a flat panel. The image data provided by a source 1 may be overlaid with other image elements when it is presented on a monitor 2.

Identifiers 12 may be any icons, marks, objects, symbols used by the system to determine what medical parameters 15 to show on the display 4. Identifiers 12 may be physical or presented on the monitor. In one embodiment, identifiers 12 may be overlaid on the image data provided by source 1 and presented on monitor 2. Identifiers 12 may also be outside the visible spectrum, for instance, in infrared. Identifiers 12 may also include medical devices or people capable of being identified, for example by using image processing software.

A controller 3 may be any processor, computer, network, or system. The controller 3 may be in communication with any of imaging source 1, monitor 2, display 4, medical device 5, and sensor 6. The controller 3 may also be integrated into any the devices in system 10 or be separate.

A display 4 may include any devices, systems or networks that display image data, or otherwise communicate image data to viewers. A display 4 may include augmented reality glasses, smart glasses, heads up displays, or wearable displays. A display 4 may also be a tablet or smartphone. A display 4 can be a single display or multiple displays.

The display 4 may have regions 14. Regions 14 may be sections of a single display 4, or multiple displays 4. Regions 14 may be different shapes, sizes, and locations, and may overlap or be distinct regions. Regions 14 may be selectable or switchable. Regions 14 may also be translucent, transparent, see-through, or removable from view when not active.

A medical device 5 can include any devices, systems, or networks that generate, acquire, store, monitor, or control status information such as patient status, device status information, or any information that may assist a medical professional. A medical device 5 may also be used to set or store user preferences for system 10. A medical device 5 can be sensors such as cardiac monitors, hemodynamic monitors, respiratory monitors, neurological monitors, blood glucose monitors, and body temperature monitors, heart rate monitors, oxygen monitors, blood pressure monitors, pulse oximeters, electrocardiograms, pressure sensors, respiratory mechanics monitors, and capnographs. A medical device 5 may also be an endoscopic camera, insufflator, or other device whose real-time status information may be helpful or safety-critical. A medical device 5 may also include any recording, storage, database, and/or archival devices or systems. A medical device 5 may also be a repository, which collects and receives patient status information from other medical devices. A medical device 5 may always communicate medical parameters to controller 3, do so selectively, or only when requested. For instance, medical devices 5 may selectively send medical parameters to controller 3 based on user preferences, which can be preset and/or modified during system use.

A sensor 6 may be used to track a view vector of display 4 or a user of the system. A sensor 6 can include any devices, systems, or networks that generate, acquire, store, monitor, or control information regarding a current orientation of display 4 or a user of the system. A sensor 6 may be a camera, video camera, or electronic device for line-of-sight imaging. A sensor 6 can also be a linear, angular, or multi-axis position sensor. Sensor 6 may be integrated into the same physical housing as display 4. For example, sensor 6 may be a camera integrated into augmented reality glasses, or a camera integrated into a tablet, or an eye tracking camera. Sensor 6 may be located outside the same physical housing as the display 4. For example, sensor 6 may be a room camera. Alternatively, sensor 6 may be an accelerometer.

Figure 2:
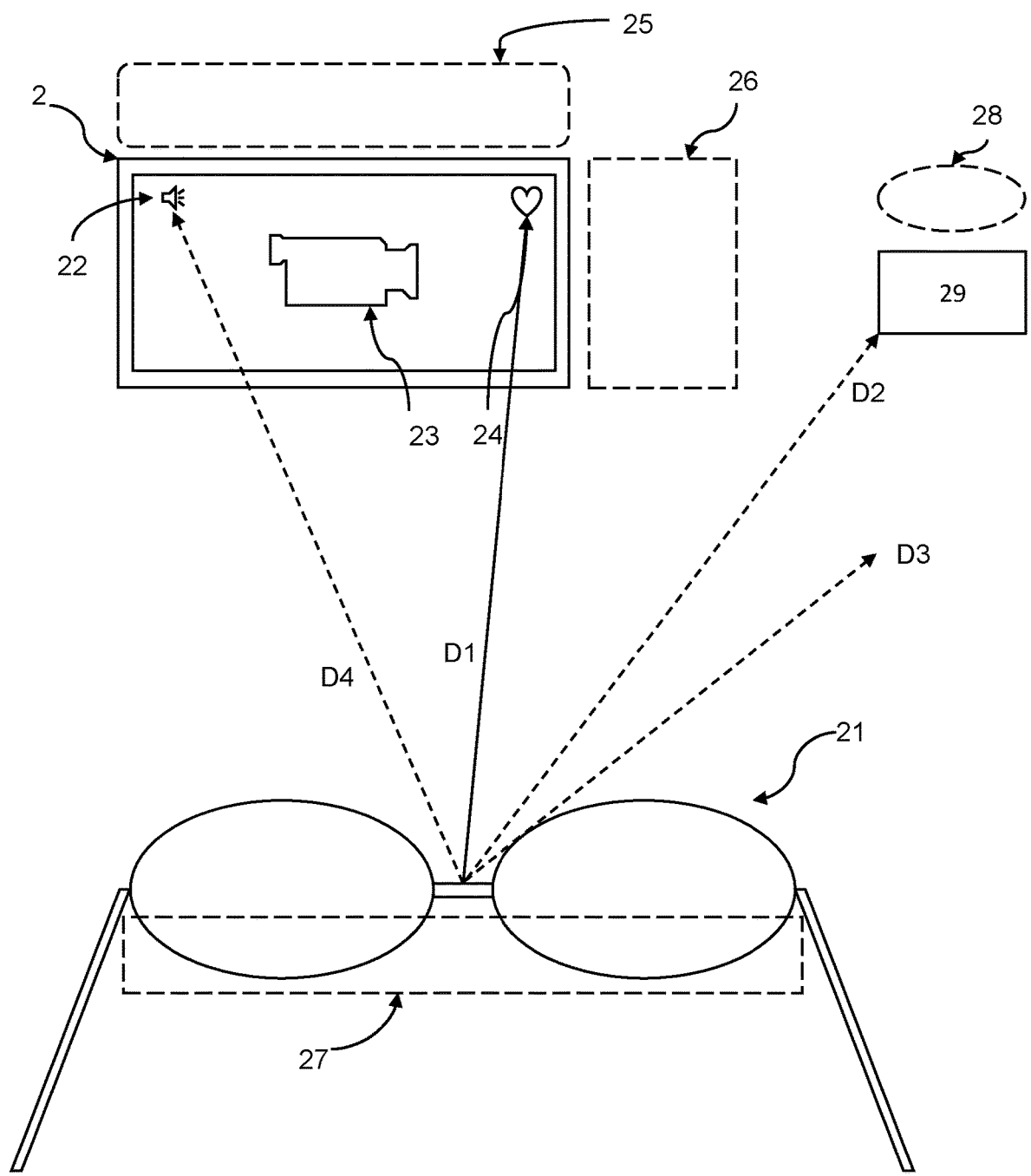
FIG. 2 is a schematic drawing of an aspect of the inventive system from FIG. 1.

Referring to FIG. 2, an embodiment of the teachings of FIG. 1 is shown. A heart rate monitor (associated with the heart-shaped icon 24) and an insufflator 28 provide medial parameters to a controller, which overlays a user interface on the image data 23 from the endoscopic camera 1 on monitor 2.

A display 4 and camera 6 are integrated in a pair of augmented reality glasses 21 which includes multiple regions. Exemplary regions 25, 26, 27, and 28 are shown in FIG. 2, though other regions of various sizes, shapes and positions may be used. Though regions 25, 26, 27, and 28 are shown in space, they are mapped to the augmented reality glasses 21, and other displays may use other mappings. As shown in FIG. 2, the multiple regions 25, 26, 27, and 28 are varied in size, shape, and location. Display regions 25 and 26 are positioned by monitor 2, while display region 28 is by insufflator 29. Display region 27 is in the periphery of the user of the augmented reality glasses' 21 vision. Regions 25, 26, 27, and 28 may be determined prior to use, or may dynamically change during use based on the view vector or medical parameters displayed.

Using images provided by camera 6, the controller determines view vectors of the augmented reality glasses 21. Three exemplary view vectors D1, D2 and D3 are shown in FIG. 2. When view vector D1 is determined, controller 3 may provide medical parameters relating to the heart rate monitor to the augmented reality glasses 21 for display because the view vector is correlated with the identifier 24 for the heart rate monitor. Based on user settings or the view vector, the medical parameters relating to the heart rate monitor may be displayed in either region 25 or 26. Additional medical parameters may be displayed based on user settings as well.

When view vector D2 is determined, controller 3 may provide medical parameters relating to the insufflator 29 to the augmented reality glasses 21 for display because the view vector is correlated with the insufflator 29. Based on user settings or the view vector, the medical parameters relating to the insufflator 29 may be displayed in region 28.

In addition, controls for the insufflator 29 may also be displayed in region 28 and selectable by the user for adjusting the medical parameters.

When view vector D3 is determined, no association is made to any medical device. Based on user settings, the medical parameters may still be displayed in the periphery region 27.

When view vector D4 is determined, the view vector is correlated with voice control icon 22. Controller 3 may activate voice control to control the system, including control of medical devices.

In another embodiment, a view vector may be correlated with a patient or an anatomy. Patient information or current patient status information may be displayed if a view vector correlated with a patient or an anatomy is determined. Controls may also be displayed if applicable. For example, if looking at a lung, biographical information about the patient, information about the patient's current oxygen levels, or information and controls relating to an endoscopic tool regarding the lung may be displayed and selectable. In addition, a view vector may cause an ideal or reference image to be displayed. The ideal or reference image may show what a body part should look like or how a body part should be aligned during surgery. Ideal or reference images may be from stock photographs or may be personalized to the patient (i.e., from previous imaging or surgeries.) In one embodiment, a surgeon may be able to follow along with ideal or reference images, which may include instructions or steps for the surgery. Furthermore, a view vector may cause a gauge to be displayed for showing information. In one example, the gauge can show a rotation of the endoscopic camera relative to the body.

As the augmented reality glasses 21 move relative to monitor 2, the relative positions, sizes and shapes of regions 25, 26, and 28 may be adjusted. For example, as view vector D1 is shortened (because the user is walking toward the monitor), region 26 may be made smaller to keep a constant size relative to monitor 2.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first", "second," etc. for different features/components of the present disclosure are only intended to distinguish the features/components from other similar features/components and not to impart any order or hierarchy to the features/components.

To aid the Patent Office and any readers of any patent issued on this application in interpreting the claims appended hereto, Applicant that it does not intend any of the claims or claim elements to invoke 35 U.S.C. 112(f) unless the words "means for" or "step for" are explicitly used in the particular claim.

While the present teachings have been described above in terms of specific embodiments, it is to be understood that they are not limited to these disclosed embodiments. Many modifications and other embodiments will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A system for displaying medical data, comprising:
a source providing image data;
a head-mounted display;
a physical monitor presenting the image data;
the physical monitor and image data being viewable without the head-mounted display, but being viewable through the head-mounted display;
a plurality of medical devices generating medical device information each indicative of a medical parameter;
a controller for determining a view vector of the head-mounted display based on data from a sensor;
wherein when the view vector is correlated with a region of the physical monitor, the head-mounted display shows the at least one piece of medical device information correlated with the view vector of the head-mounted display.

2. The system of claim 1, wherein a correlation of the view vector is achieved by aligning a vector extending perpendicular from the head-mounted display with an object.

3. The system of claim 1, wherein the at least one piece of medical device information is related to patient status information.

4. The system of claim 1, wherein the at least one piece of medical device information is related to device status information.

5. The system of claim 1, wherein the at least one piece of medical device information is related to device control.

6. The system of claim 5, wherein the at least one piece of medical device information includes a menu.

7. The system of claim 6, wherein the menu allows control of at least one of the plurality of medical devices based on the view vector of the head-mounted display.

8. The system of claim 1, wherein the view vector is correlated with an anatomy on the monitor.

9. The system of claim 8, wherein the at least one piece of medical device information is related to the anatomy.

10. The system of claim 1, wherein the view vector is correlated with an icon on the monitor.

11. The system of claim 1, wherein the at least one piece of medical device information is related to the medical device associated with the icon.

12. The system of claim 1, wherein the view vector is correlated with a medical device.

13. The system of claim 12, wherein the at least one piece of medical device information is related to the medical device.

14. The system of claim 1, wherein user input is used to determine which at least one piece of medical device information to display.

15. The system of claim 1, wherein the display can be worn by a user.

16. The system of claim 1, wherein the display is provided as glasses or goggles.

17. The system of claim 1, wherein the sensor is a camera and the data is an image.

18. The system of claim 1, wherein the sensor is a position sensor.

19. The system of claim 1, further comprising:
a plurality of regions of the display;
the controller determining in which region of the display to present at least one piece of medical device information corresponding to the view vector of the display.

20. The system of claim 19, wherein a region of the display is in a periphery of a view vector of a user of the system.

21. The system of claim 19, wherein an area of at least one of the plurality of regions is determined based on a view vector of a user of the system.

22. The system of claim 1, wherein the source is an endoscopic camera and the physical monitor is a surgical monitor.

* * * * *